(12) United States Patent
Galiano

(10) Patent No.: US 8,679,739 B2
(45) Date of Patent: Mar. 25, 2014

(54) METHOD AND APPARATUS FOR DIAGNOSTIC ANALYSES

(75) Inventor: Paolo Galiano, Padua (IT)

(73) Assignee: Alifax Holding SpA, Polverara (IT)

( * ) Notice: Subject to any disclaimer, the term of this patent is extended or adjusted under 35 U.S.C. 154(b) by 0 days.

(21) Appl. No.: 13/522,251

(22) PCT Filed: Jan. 13, 2011

(86) PCT No.: PCT/IB2011/000056
§ 371 (c)(1),
(2), (4) Date: Jul. 13, 2012

(87) PCT Pub. No.: WO2011/086462
PCT Pub. Date: Jul. 21, 2011

(65) Prior Publication Data
US 2013/0022962 A1    Jan. 24, 2013

(30) Foreign Application Priority Data
Jan. 14, 2010   (IT) .................................. 2010A0003

(51) Int. Cl.
*C12Q 1/00* (2006.01)
*C12Q 1/70* (2006.01)
*C12M 1/00* (2006.01)

(52) U.S. Cl.
USPC ................. 435/4; 435/5; 435/283.1

(58) Field of Classification Search
None
See application file for complete search history.

(56) References Cited

U.S. PATENT DOCUMENTS

| 5,356,815 A | 10/1994 | Ciotti |
| 2005/0254055 A1 | 11/2005 | Peng |
| 2007/0269853 A1 | 11/2007 | Galiano |
| 2011/0151503 A1 | 6/2011 | Galiano |
| 2011/0307183 A1 | 12/2011 | Galiano et al. |

FOREIGN PATENT DOCUMENTS

| IT | 1259750 | 3/1996 |
| IT | 2008A0190 | 2/2010 |
| IT | 2009A0048 | 8/2010 |
| WO | 2009/065580 | 5/2009 |

OTHER PUBLICATIONS

Roessler et al., "Permanent turbidty standards," Applied Microbiology, 1967, vol. 15, No. 5, pp. 1114-1121.

*Primary Examiner* — Albert Navarro
(74) *Attorney, Agent, or Firm* — Hamre, Schumann, Mueller & Larson, P.C.

(57) ABSTRACT

A method for diagnostic analysis, in particular to identify pathogens, such as viruses, bacteria or other micro-organisms present in a biological sample, comprises a first step of measuring and continuously monitoring the turbidity and/or the concentration of the pathogens, by means of an instrumental reading technique, of a liquid culture medium into which the sample to be analyzed has been inoculated and in which the replication of the pathogens possibly present occurs, said measuring and monitoring being carried out dynamically during the replication of the pathogens growing in the culture medium; and a second step of identifying the pathogens, carried out by taking at least an aliquot of the liquid culture medium containing the biological sample directly obtained from the first step, which has reached a desired value of turbidity according to a standardized value scale, such as the McFarland turbidity scale, and/or of concentration of the pathogens, and using said aliquot directly in mass spectrophotometric identification means (15) in order to identify the pathogens, which means are calibrated in their functioning depending on the measurement results of the first step. The desired values of turbidity and/or of concentration of the pathogens are preliminarily selected, during the first step, on the basis of the specific needs which, on each occasion, are identified in order to carry out the second identification step.

13 Claims, 1 Drawing Sheet

METHOD AND APPARATUS FOR DIAGNOSTIC ANALYSES

FIELD OF THE INVENTION

The present invention concerns a method and apparatus for diagnostic analyses, in particular to identify pathogens, such as viruses, bacteria or other micro-organisms by means of mass spectrophotometric measurements.

BACKGROUND OF THE INVENTION

It is known that an in vitro sensitivity test to antibiotics (antibiogram) provides, on the basis of current international guide lines, to set up a standardized bacterial suspension to test against optimized concentrations (breakpoints) or scale dilutions of antibiotics (M.I.C).

The number of bacteria analyzed must be standardized irrespective of the sensitivity of the method adopted for the test.

The preparation of an inoculum is one of the most critical passages in every sensitivity test or antibiogram. The inoculum can significantly influence the dimensions of the inhibition area.

The choice of the inoculum method is mainly conditioned by practical considerations, but the results are better if some form of standardization is adopted, such as the comparison of the density of the suspension of the micro-organisms to a determinate standard of turbidity or to an equivalent latex, or by making photometric measurements.

In particular, the standardization method most widely used for the standardization of the inoculum uses the McFarland turbidity standard, typically used in microbiology as a reference to regulate the turbidity of bacterial suspensions so as to have the number of bacteria within a certain range.

It is known that, in classical microbiology, McFarland turbidity is the usual one to be able to begin tests on antibiotics (antibiogram) or to perform a phenotypical identification. Normally, the growth in a Petrie dish shows the isolated colonies and these bacteria are diluted until the McFarland value of 0.5 is obtained, that is, the level of turbidity.

The McFarland standards (0.1, ..., 0.3, ..., 0.5, ..., 1, ..., 2, ..., 3, ..., 4, ...) can be prepared by means of the addition of specific volumes of sulfuric acid and barium chloride dehydrate to obtain a solution of barium sulfate with a specific optical density.

The most common standard used is the McFarland 0.5 standard which supplies a visually comparable standard with that of a bacterial suspension, in a sterile saline solution or growth broth, containing approximately $1.5*10^8$ CFU/ml.

Once standardized, the suspension of the inoculum should be used within 15 minutes of the preparation.

The application UD2009A000048 in the name of the Applicant proposes a method to rapidly obtain a standardization of McFarland turbidity, to be combined with the execution of a direct antibiogram. This method is particularly useful for patients affected by the presence of bacteria in biological liquids and in urine in particular, and to begin the antibiotic therapy quickly.

The application US-A-2005/254055 is also known which describes a method to monitor the cellular growth and the concentration in a dynamic environment of cell cultures.

As an alternative bacterial identification technique it is also known, for example from the international application WO-A-2009/065580 (WO'580), to carry out the identification of pathogens, such as viruses, bacteria or other micro-organisms, by means of mass spectrophotometric measurements of their protein profile, obtained from pathogens directly precipitated as pellets from biological fluid samples centrifuged after culture growth in a defined solid growth medium, for example a solid medium in a Petrie dish. The growth of bacteria in a Petrie dish normally occurs in a time which varies from six to twenty hours. In such culture media even contaminating bacteria can grow, and in any case the identification method, in order to be applied to the mass spectrophotometer, must bear in mind that:

the mass of bacteria of the pellet is put into contact with a conventional matrix to ionize the sample and must come within a range of Daltons which varies from 3,000 to 15,000 Daltons, with a Dalton mass minimum equal to 2,500. Values above this range risk blocking the mass spectrophotometer.

It must also be noted that the pellet obtained from the positive sample with the method described in WO'580 does not allow to select the pollutants from the bacteria responsible for the infection in progress.

Consequently, WO'580 has its limitations in discriminating a maximum of two bacteria in the sample to be analyzed, in that the detection algorithm to identify the bacteria using an identification library is not able to discriminate if the number of bacteria present in a sample is more than the two species combined. Consequently the known technique suffers in particular from the presence of other contaminating bacteria, as well as the bacterium responsible for the infection.

Moreover, this technology can often give mass spectrums which are not very clear with problems of basic interference. Furthermore, the centrifugation method contributes to lengthening the times and increases the overall costs of analysis.

Purpose of the present invention is to perfect a method and achieve an apparatus for diagnostic analyses, in particular to identify pathogens, such as bacteria, viruses or other micro-organisms, which is both quick, economical, reliable, even in the case of the presence of other contaminating pathogens as well as the pathogens responsible for the infection, and which simplifies a subsequent identification step by means of mass spectrophotometry.

The Applicant has devised, tested and embodied the present invention to overcome the shortcomings of the state of the art and to obtain these and other purposes and advantages.

SUMMARY OF THE INVENTION

The present invention is set forth and characterized in the independent claims, while the dependent claims describe other characteristics of the invention or variants to the main inventive idea.

The present invention takes as its basis the pathogens identification technology described in the international application WO-A-2009/065580, wholly incorporated here as reference.

Moreover, the present invention is based on the measurement of the turbidity of a culture medium containing a sample in which there is a replication of the pathogens, by means of the McFarland scale, as described in the application UD2009A000048 in the name of the Applicant and wholly incorporated here as reference, and the determination of the pathogen load, in the case of bacterial load calculated in CFU (colony forming unit), as described in the Italian patent IT-B-1.259.750 and in the Italian patent application UD2008A000190 in the name of the Applicant, both wholly incorporated here as reference.

In particular, in the application UD2009A000048 a desired value of turbidity is given, in order to carry out the direct antibiogram, from the same biological sample in a growth step to be used in a subsequent identification step of the bacteria in the growth step.

In particular, in the application UD2009A000048 a light-scattering reading is carried out in order to determine the turbidity according to the McFarland standard of a suspension formed by a liquid culture medium, or eugonic broth, into which the biological sample has been inoculated and in which the turbidity is measured continuously directly from the suspension of the sample under analysis during the growth step of the bacteria, until a determinate threshold is reached, expressed according to the McFarland standard, generally the value 0.5.

According to a feature of the present invention, therefore, a method for diagnostic analyses according to the present invention, in particular to identify pathogens, such as viruses, bacteria or other micro-organisms present in a biological sample, comprises:

- a first step of measuring and continuously monitoring the turbidity and/or the concentration of the pathogens, that is, counting the pathogens present in the sample examined, expressed in CFU in the case of bacterial count by means of an instrumental reading technique, preferably by means of light scattering technology, or in some forms of embodiment, also by means of photometry or other optoelectronic technologies, or based on radio frequencies or even ultrasounds, of a liquid culture medium, advantageously specific and selective to the growth of the pathogens to be analyzed, into which the sample to be analyzed has been inoculated and in which the replication or growth of the pathogens possibly present occurs, said measuring and monitoring being carried out dynamically during the replication of the pathogens growing in the liquid culture medium; and
- a second step of identifying the pathogens, carried out by taking at least an aliquot of the liquid culture medium containing the biological sample directly obtained from the first step, which has reached a desired value of turbidity, caused by the replication of the pathogens in progress and/or a desired value of concentration, or count, of the pathogens according to a scale of standardized values, such as the McFarland turbidity scale, and/or the concentration of the pathogens, expressed in CFU in the case of the bacteria and using said aliquot directly in mass spectrophotometric identification means in order to identify the pathogens, which means are calibrated in their functioning depending on the measurement results of the first step.

According to the present invention, the desired value of turbidity and/or the value of concentration, or count, of the pathogens are preliminarily selected during the course of the first step, on the basis of the specific needs which, on each occasion, are identified in order to carry out the second identification step by means of mass spectrophotometry.

In some forms of embodiment, the second identification step is carried out manually, while in other forms of embodiment the second step is carried out automatically, providing a suitable automatic taking and transport of the sample at the desired McFarland turbidity.

Advantageously the time needed to obtain the desired value of turbidity and/or relative concentration or count of the pathogens in the first step is such that the subsequent second identification step is independent from the possible presence of contaminating pathogens in the sample.

Advantageously the time needed to obtain the desired value of turbidity and/or relative concentration or count of the pathogens in the first step is comprised between 45 minutes and 3 hours, even more advantageously less than 1 hour, and the sample is used within 3 hours, to avoid the influence of contaminants in the analysis.

Another feature of the present invention concerns an apparatus for diagnostic analyses, in particular to identify pathogens, such as viruses, bacteria or other micro-organisms present in a biological sample, which apparatus comprises:

- means for measuring and continuously monitoring the turbidity and/or the concentration of the pathogens, or count of the pathogens in the sample being tested, expressed in CFU in the case of the bacterial count, preferably by means of light scattering technology, or in some forms of embodiment even by photometric means, or other optoelectronic technologies, or based on radio frequencies or even ultrasounds, of a liquid culture medium into which the sample to be analyzed has been inoculated and in which the replication of the pathogens possibly present occurs; and
- mass spectrophotometric identification means able to identify the pathogens in at least one aliquot of the liquid culture medium containing the biological sample, which has reached a desired value of turbidity, caused by the replication of the pathogens in progress, and/or of concentration or count of the pathogens according to a standardized scale, such as the McFarland turbidity scale and/or the concentration of the pathogens, expressed in CFU in the case of the bacterial count; the mass spectrophotometric identification means are calibrated, in their functioning, on the basis of the results of the measurement of the turbidity and/or concentration of the pathogens obtained by the measuring and monitoring means. The measuring and monitoring means comprise processing means provided with memorization means in which are memorized first data relating to a predefined graduated progression of said turbidity values, together with or in alternative to the measurement values of the concentration or count of the pathogens, and second data relating to a defined correlation between said turbidity values and/or concentration or count of the pathogens and ranges of values of weight from the sample which is loaded in them, selected to be suitable for the functioning of the mass spectrophotometric identification means.

The processing means are able to select said desired value of turbidity and/or concentration of the pathogens, expressed in CFU in the case of the bacterial count, from among said first data on the basis of one of the values contained in said second data which is selected on each occasion on the basis of the specific needs of said mass spectrophotometric identification means.

The measuring and monitoring means are configured so that the time needed to obtain the desired turbidity value and/or relative concentration of pathogens is such that the identification by the mass spectrophotometric identification means is independent from the possible presence of contaminating pathogens in the sample.

An advantage of the preliminary step of light-scattering measuring or other technology which can be used for this purpose, is that the level of turbidity is suitably measured and selected eliminating possible factors of disturbance by means of a differential measurement of the turbidity from the moment of its inoculation into the liquid growth medium. A basic turbidity is therefore measured. Jointly, for each sample, the counts of the pathogens can be expressed to support the detection of the turbidity measured.

A basic reading of the sample to be analyzed for the presence of bacteria or other pathogens allows to subtract such factors of disturbance, with respect to subsequent reading values of the turbidity which can be attributed exclusively to the active replication of the virulent bacteria and which constitute turbidity connected to the quantity in weight of the growing mass of bacteria.

The growth in a liquid medium allows to highlight growths by measuring the turbidity, with the possible simultaneous measurement of the count of the pathogens coupled to the turbidity detected, even at very low initial values of growth, and therefore gives suitability to the sample which is becoming positive in a very short time, equal to a range of between about 45 minutes and about 3 hours and guaranteeing, by measuring the turbidity, the values of weight in Daltons required by the mass spectrophotometer for identification.

These turbidity values, obtained even after only 45 minutes incubation, allow to begin the identification of the bacterium or other pathogen giving a sample with the suitability required by a mass spectrophotometer.

The McFarland measurement using light-scattering technology or other suitable techniques, gives turbidity equivalent to the mass in Daltons considered critical for the subsequent analysis of mass spectrophotometry.

The use of light-scattering technology during the preliminary step of the culture is preferential in that its high sensitivity properties allow a rapid detection of the optimal level of turbidity for the subsequent identification step with the mass spectrophotometer and therefore greater acceleration of work times. However, more generally, other suitable techniques can equally be used, such as nephelometric laser techniques, or photometric reading systems or other systems of turbidity detection, such as optoelectronic or radio frequency or ultrasounds, normally used in the field of instrumentation of the diagnostic-laboratory type.

The present invention thus allows to use the positivized sample growing in a liquid culture medium and standardized to a desired McFarland turbidity value correlated to a determinate weight in Daltons, in any mass spectrophotometer.

The present invention even overcomes the problem of contaminating bacteria and of the presence of several bacterial species in the sample.

It is known that the replication steps of the bacteria in a sample, for example of urine inoculated into a liquid eugonic broth, manifest themselves with the increased turbidity of the sample. The dynamic McFarland evaluation allows to detect the increased turbidity right from the first bacterial replications and the results of possible positivity are advantageously obtained after only 45 minutes of incubation.

In this first step, it is the bacteria responsible for the infection which, as they replicate, cause increased turbidity. Instead, the contaminating bacteria collected during the taking of the sample take time to adapt to the new environment in the urine sample and therefore manifest their growth only after a few hours.

A typical example is that of the bacteria resident in the urogenital apparatus, for example coagulase negative *Staphylococcus*, which are accidentally collected during the taking of the urine sample and therefore can show a growth on conventional culture media.

Another example, in the case of taking respiratory samples, can be the presence of *Streptococcus* or non-pathogen *Streptococcus* in the saliva, or yeasts or other polluting organisms.

In some forms of embodiment, the present invention provides to measure the turbidity of a biological sample, in particular of a liquid culture medium into which the biological sample is inoculated, preferentially by means of light-scattering technology or other equivalent or alternative suitable technique, in a window of McFarland turbidity values which goes from 0.1 to 10, for the purposes of a subsequent identification step of the bacteria by means of mass spectrophotometry. The level of turbidity is proportionate to the threshold needed for the spectrophotometric analysis to be carried out, giving thresholds of values in CFU equal to $10^2$, $10^3$, $10^4$, $10^5$, $10^6$, etc.

In particular, knowing the relation between McFarland turbidity values and weight in Daltons, it is possible to regulate the McFarland turbidity of the growing sample in correspondence with the weight range 3,000-15,000 Daltons, optimal for the spectrophotometric measurement in question. Indeed, knowing that a mass spectrophotometer has to be fed by liquid substances suitable for the recognition of protein ions, in a weight range of 3,000-15,000 Daltons, the turbidity measurer can be adjusted to give notice that a correlated value of McFarland turbidity has been reached, depending on the optimization of the sample to be analyzed, and also to supply, at the same time, the count of the pathogens in replication which cause the variation in turbidity, avoiding having to use, during an automatic work cycle, excessively turbid samples and therefore outside the optimal range, more than 15,000 Daltons or less than 2,500 Daltons. Consequently, the dynamic monitoring of the McFarland turbidity value allows to load samples in which there is a bacterial load within the optimal limits required by the mass spectrophotometry instruments, in order to avoid blocking the instrument.

The present invention therefore allows to use a growth medium in a liquid form measured at a variable McFarland turbidity as required, so that the sample can be inserted in a mass spectrophotometer to obtain the identification of the sample.

The method developed according to the present invention is able to supply turbidity values of samples positive to culture growth, excluding the growth of contaminating bacteria. This solves the problem expressed by WO'580 when there are more than two bacterial species in the same sample to be analyzed. This is because, since the so-called lag phase in the growth of the contaminants due to the adjustment of said contaminants to the new growth environment is known, the dynamic measurement of the necessary turbidity value allows, given the rapid times as discussed above, to obviate the limitation described in WO'580.

The present invention allows to overcome the concentration step on pellets as described in WO'580 and therefore to be able to simplify and speed up the identification step compared with WO'580, using the growing sample directly, with the suitable McFarland turbidity value.

In some forms of embodiment of the present invention, it is provided to select the biological samples growing in a culture medium which express determinate McFarland turbidity values, depending on the mass measurement in Daltons to be used in the mass spectrophotometer, normally comprised between 3,000 and 15,000 Daltons.

The McFarland turbidity measurer, using light-scattering technology or other suitable technique, can be set with a scalar reading program to different McFarland turbidities, 0.1, . . . , 0.2, . . . , 0.3, . . . 0.5, . . . etc., to avoid reading mixed load samples, inasmuch as, as already explained, if the load has two bacteria, normally the known mass spectrophotometric system still works well, however, if there are three or more bacteria, the response would no longer be trustworthy.

Since the polluting bacteria take a certain period of time to adapt in a test tube or bottle where the sample, for example urine, has been inserted, as they are no longer in their natural growth environment, they begin to replicate after 3 hours of growth, normally after 4 to 5 hours, and therefore the method proposed is affected little or not at all by contaminating bacteria and by the false positivity deriving therefrom, since it considers the first 45 minutes of fast replication in the course of which the desired McFarland value is reached, in combination with or alternative to the growth graph of the pathogens in the exponential phase. In fact, it is possible to determine the load of bacteria in a high replication phase in only 45 minutes, distinguishing the bacteria that cause the infection, with great vitality of the possible polluting bacteria that require a longer adaptation time.

Therefore the identification of scalar McFarland value 0.1, ..., 0.5, ... etc., can provide a secure identification of only the bacteria responsible for the infection, for example in the urogenital tract in the case of urine samples, given that, as we have said, they are the first to replicate.

The present invention allows to automate the subsequent identification step, since the exponential growth of a bacterial load inside a liquid culture broth container with inoculated substance, such as urine or other biological liquid, provides a control and certain and programmable data in order to carry out the identification by means of mass spectrophotometry with the preselected desired turbidities.

Compared to WO'580, in which the best results are obtained with a pure colony of bacteria and up to two bacteria present (from three colonies of bacterial species or more the trustworthiness of the results declines rapidly), the present invention allows to operate without obtaining the pure colony, in that, usually, the active measuring of the replication by means of the McFarland turbidity measurement can be identified, within the first 3 hours, mainly for mono-microbial cultures. For example, for urinary samples, 70% of the pathologies are supported by mono-microbial growths and 15% have two microbial species.

With particular reference to the possible existence of polymicrobial growths, a rapid culture step in liquid as in UD2009A000048, stopped at the moment of detection by the system, by a determinate McFarland turbidity value reached, allows to subject the sample to the identification test using mass spectrophotometry during the first logarithmic growth step of the possible bacteria present, therefore in an early step. This means that the predominant pathogen will be overexposed and the other bacteria present, if contaminant and therefore not in a logarithmic step, will remain latent and can therefore be totally negligible in terms of absolute concentration at the moment of the spectrophotometric analysis, and they will not interfere with the analysis of the protein or lipidic profiles on which the mass spectrophotometric identification system is based.

The same improvement can be applied to the interferences which, at sample level, disturb the detection of the profiles by the system, as occurs in WO'580.

Moreover, the use of selective liquid culture media during the culture step previous to the mass spectrophotometric identification could further improve the performance of the spectrophotometer.

Indeed, using selective media or media to which selective substances have been added, for example antibiotics or others, the culture step can also act as a pre-selection element of determinate micro-organisms or particular determinate subspecies of micro-organisms, for example *Staphylococcus aureus* MRSA, which the mass spectrophotometer identification system is not able to identify directly or to differentiate in a satisfactory manner, without the use of selective growth media. The step of growth in a selective culture medium is therefore a diagnostic instrument that assists and improves the identification technique by means of the mass spectrophotometer.

Therefore, the measurement of turbidity using a light-scattering technique or other alternative and similar technique, preliminary and preparatory to the subsequent identification of the pathogens by means of mass spectrophotometry, allows:

to use the same sample, or an aliquot thereof, expressed as positive to the culture growth in a eugonic culture medium in liquid phase for subsequent identification by means of mass spectrophotometry;

the possible use of the same sample avoiding the pelletization step by centrifugation of the positive sample;

to avoid the pelletization step by centrifugation of the positive sample;

to provide a McFarland value and/or a result of the pathogen count, expressed in terms of CFU in the case of bacteria, suitable and equivalent to an optimal range of 3,000-15,000 Daltons for subsequent mass spectrophotometry, in order to avoid the use of excessively turbid samples and to prevent possible blocking of the mass spectrophotometer;

to exclude from the analysis the growth of contaminating bacteria at the sample taking step, if used within, typically, the 3 hours of growth;

to provide the mass spectrophotometer with a sample without contaminants if used within the stated 3 hours of growth;

to provide positive samples for the range of turbidity values required and considered suitable for the use of the mass spectrophotometer, typically 0.1, 0.25, 0.5, 0.75, 1.00, 1.25, 1.5, 1.75, 2.00, 2.22, 2.5 etc., with simultaneous display of the pathogens count too, in the case of bacteria expressed in CFU, to identify, by means of the mass spectrophotometer, the presence of active and contaminating replicating pathogens up to two bacteria in the same sample, as well as the pathogens responsible for the infection;

to prepare positive samples with McFarland turbidity values equivalent to the minimum which can be determined, that is, 2,500 Daltons, detected by the mass spectrophotometer;

to determine a correlation between the turbidity measurement according to the standardized McFarland scale, and possibly the pathogen count, expressed in CFU in the case of bacteria, and molecular weights suitable for detection by the mass spectrophotometer;

in some forms of embodiment, to use selective liquid culture media able to detect bacteria which are difficult to interpret by using specific libraries (for example *Staphylococcus aureus* MRSA), obtaining an adequate response from the mass spectrophotometer.

The dynamic measurement of standard turbidity, typically of the McFarland scale, set for suitable pre-chosen turbidity targets and possibly the pathogen count, expressed in CFU in the case of bacteria, renders the sample analyzed suitable to carry out the rapid identification which can be obtained using a mass spectrophotometer, so that in an automatic detection process of the pre-chosen turbidity, an automated work system can be provided, which is quick and does not have the problems that interfere with identification as described by WO'580.

The dynamic reading of the McFarland turbidity of a sample in sequential times also allows to verify the identification by means of mass spectrophotometry for the presence of contaminating bacteria after the initial incubation time (from about 45 minutes to about 3 hours), with respect to identification after ⅘ hours of incubation of the same sample analyzed.

By suitably covering the viruses or other micro-organisms with lipidic substances or specific lactics, the present invention is also suitable for virological and not only bacterial identification.

The use of selective liquid culture media for the growth of difficult bacteria or media suitable for the growth of some bacteria of particular interest also comes within the field and scope of the present invention.

BRIEF DESCRIPTION OF THE DRAWINGS

These and other characteristics of the present invention will become apparent from the following description of a preferential form of embodiment, given as a non-restrictive example with reference to the attached drawings wherein.

Figure 1:
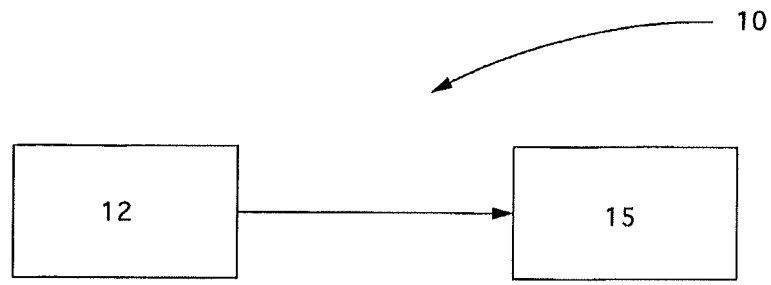
FIG. 1 is a schematic representation of an apparatus for diagnostic analyses according to the present invention.
Figure 2:
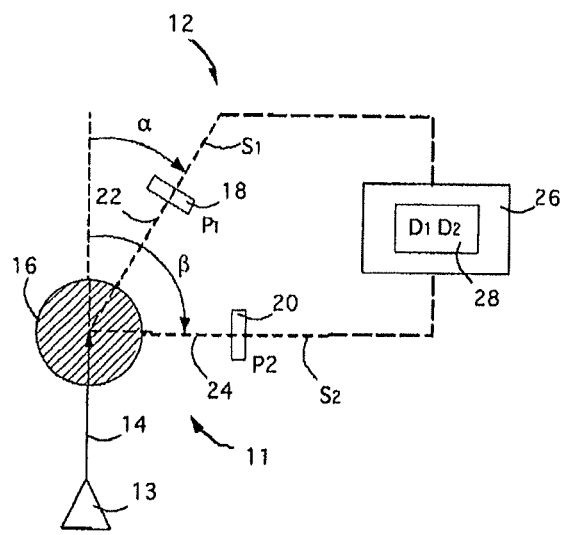
FIG. 2 is a schematic representation of a part of the apparatus in FIG. 1.
Figure 3:
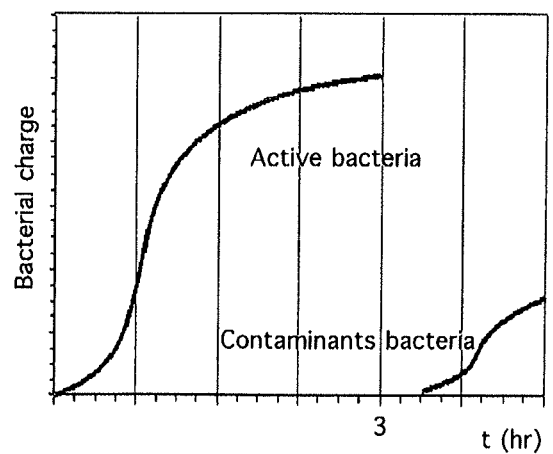
FIG. 3 is a graph of the development of the bacterial load over time.

To facilitate comprehension, the same reference numbers have been used, where possible, to identify common elements in the drawings that are substantially identical. It is understood that elements and characteristics of one form of embodiment can conveniently be incorporated into other forms of embodiment without further clarifications.

DETAILED DESCRIPTION OF A PREFERENTIAL FORM OF EMBODIMENT

With reference to the attached drawings, a method according to the present invention provides to prepare, by means of light-scattering technology, a biological sample in replication in liquid culture broth, or eugonic broth, at a desired defined McFarland turbidity value, and subsequently to use the sample prepared, or an aliquot thereof, in a mass spectrophotometry measurement intended to identify possible pathogens present. Although it refers, in a non-restrictive manner, to the light-scattering technology, the present invention can also provide other similar techniques, as indicated above.

In this case, the method uses an apparatus 10 (FIG. 1) which comprises a light-scattering measuring device 12 and a mass spectrophotometer 15, for example of the MALDI (Matrix Assisted Laser Desorption) type.

The device 12 provides to use a containing element or test tube 16, transparent to electromagnetic radiations inside which the bacterial growth of a suspension of the biological sample inoculated in the eugonic broth is provided.

The device 12 comprises a reading unit 11 by means of which the light diffused by the suspension contained in the test tube 16 is detected, and processing means 26, such as a computer, by means of which the signals received by the reading unit 11 are processed for the purposes of the analysis.

With the present invention, the sample is subjected to a culture test in order to verify its positivity to possible pathogen micro-organisms, for example to a determinate bacterial strain, and, if positive, one prepared to the desired turbidity and pathogen concentration, is used directly in subsequent bacterial identification steps.

The measurement of the McFarland turbidity of the sample in the test tube by means of the reading unit 11 in FIG. 1 is based, in this case, on the emission of laser light and light-scattering reading, directly in the analysis step, that is, at the same time as the bacterial growth during the culture test in order to determine the bacterial load in the sample under analysis.

In particular the reading unit 11 is provided with emitter means 13 by means of which a beam 14 of coherent, polarized (laser) and collimated light is made to strike the test tube 16.

Moreover, the reading unit 11 comprises sensor means, first 18 and second 20, by means of which a detection over time of rays 22, 24 of light diffused or refracted by the suspension is carried out.

The first 18 and the second 20 sensor means are able to generate corresponding signals S1, S2 which are transmitted to the processing means 26.

The biological samples, with the presence of duplicating bacteria, emit signals of diffused light which the reading unit 11 then detects and the processing means 26 process in order to provide specific curves which express the development of the bacterial growth over time.

The first 18 and the second 20 sensor means are located in correspondence with a first P1 and a second P2 angular position (FIG. 1), different from each other, with respect to the test tube 16, so as to determine a first $V1(t)$ and a second $V2(t)$ curve, respectively associated with the first P1 and the second P2 angular position, of the development over time of the turbidity of the bacterial suspension.

In this case, the first 18 and the second 20 sensor means are positioned at two pre-established angles $\alpha$ and $\beta$ with respect to the direction of the beam 14, for example at 30° and 90° respectively (FIG. 1).

The processing means 26 comprise memorization means 28 with a database in which data D1 and D2 are memorized, which respectively concern progressive scale values of McFarland turbidity and conversion values from the McFarland turbidity scale to weight in Daltons, so as to be able to correlate the McFarland values at which the samples are prepared with the optimal weight range used by the mass spectrophotometer 15. The time taken to reach a pre-established level of McFarland turbidity, for example 0.5, of the sample during the growth step depends on the initial bacterial load of the sample, where the greater the count value, the quicker the pre-established McFarland threshold will be reached.

The reading unit 11, in conjunction with or as an alternative to reaching the desired McFarland value, is also able to count the pathogen micro-organisms possibly present, expressed in CFU in the case of the bacteria. Indeed, the optical measurement which is carried out, in this case of the nephelometric type based on light-scattering technology, gives a quantitative measurement of the bacterial count, based on an exponential development as a function of time.

In particular, the radiations detected by the sensors 18 and 20 are converted into electric signals and then sent to the processing means 26 which provide to process the data and to calculate the results.

The bacterial growth curve is compared with reference values comprised in a database of the processing means 26 so as to determine the analysis parameters, such as the quantity and the replication speed of the micro-organisms present in the sample.

The calculation method is based on the fact that the bacterial growth inside the suspension causes the variation over time of the intensity of the diverted light.

Periodic readings of the diverted radiation allow to construct, by means of known interpolation methods, the growth curve of the bacterial colonies inside the plasma sample being tested, said curve relating to the angle of detection in which the detector is positioned.

It has been experimentally demonstrated that the growth curve has an exponential progress as a function of time, such as $C_B = Ae^{K_n(t-t_0)} + C$.

In the formula, $C_B$ represents the intensity of the diverted radiation, A and C are constants respectively depending on the bacterial species being tested and on the initial concentration, $K_n$ is a parameter which takes into account the positioning angle of the detector, t is the time and $t_0$ is a delay connected to the number of bacteria present in the sample.

The combined determination of the desired McFarland turbidity and pathogen count is advantageous, in particular, in the case where the liquid medium with the replicating sample is too turbid, and therefore the quantitative determination of the pathogens using the McFarland scale could be difficult, while the quantification using the growth curve could be more reliable, or, in the opposite case, where it is too little turbid. Once the sample has been prepared, it or an aliquot thereof is transferred to the mass spectrophotometer 15 which proceeds with the identification of the pathogen. The constructive and functioning details of the mass spectrophotometer 15 are known, for example from WO'580, and are not described here.

The invention thus allows to choose the concentration of micro-organisms and/or the turbidity desired and determined by the increase in bacterial mass in its incubation step, connected to the subsequent identification step obtained by means of the mass spectrophotometer.

It is clear that modifications and/or additions of parts may be made to the apparatus 10 and method for diagnostic analyses as described heretofore, without departing from the field and scope of the present invention. It is also clear that, although the present invention has been described with reference to specific examples, a person of skill in the art shall certainly be able to achieve many other equivalent forms of apparatus and method for diagnostic analyses, having the characteristics as set forth in the claims and hence all coming within the field of protection defined thereby.

The invention claimed is:

1. A method for diagnostic analyses to identify pathogens including viruses, bacteria or other micro-organisms present in a biological sample and responsible for an infection, comprising:
    a first step of measuring and continuously monitoring a turbidity and/or a concentration of pathogens in a liquid culture medium into which a biological sample to be analyzed has been inoculated and in which a replication of the pathogens possibly present occurs, wherein an instrumental reading technique is used to measure and continuously monitor the turbidity and/or the concentration of the pathogens, and said measuring and monitoring are carried out dynamically during the replication of the pathogens growing in the culture medium; and
    a second step of identifying the pathogens by taking at least an aliquot of the liquid culture medium containing the biological sample directly obtained from the first step, which has reached a desired turbidity value according to a standardized value scale, and/or of a desired concentration of the pathogens, and using a mass spectrophotometric identification technique to identify the pathogens in the aliquot, wherein the mass spectrophotometric identification technique involves calibration depending on the measurement results of the first step;
    wherein during the first step, said desired turbidity value and/or the desired concentration of the pathogens is preliminarily selected on the basis of the specific needs which, on each occasion, are identified in order to carry out the second identification step, and
    wherein in the first step, a time needed to obtain a desired turbidity value and/or a desired concentration of the pathogens is shorter for pathogens that are responsible for the infection than that of other contaminating pathogens, and a time needed for pathogens to adapt to the environment in said biological sample and to manifest growth is shorter for the pathogens that are responsible for the infection than that of the other contaminating pathogens such that the identification in the second step is independent from the presence of said other contaminating pathogens in the biological sample.

2. The method as in claim 1, wherein the time needed to obtain the desired turbidity value and/or the desired concentration of the pathogens in the first step is calculated based on a known lag phase in a growth of said other contaminating pathogens in the biological sample due to an adjustment of said other contaminating pathogens to a grown environment in said biological sample.

3. The method as in claim 1, wherein the biological sample brought to the desired turbidity value and/or the desired concentration of the pathogens in the first step is used within 3 hours of performing the second step.

4. The method as in claim 1, wherein the first step is able to supply turbidity values of the biological sample corresponding to a range between 3,000 and 15,000 Daltons of weight of the biological sample to be identified in the second step.

5. The method as in claim 1, further comprising in said first step, providing a selective liquid culture media, or media to which selective substances are added, for the growth of a desired pathogen.

6. An apparatus for diagnostic analyses to identify pathogens including viruses, bacteria or other micro-organisms present in a biological sample and responsible for an infection, comprising:
    an apparatus that is configured to measure and continuously monitor a turbidity and/or a concentration of pathogens, using an instrumental reading technique, in a liquid culture medium into which the biological sample to be analyzed has been inoculated and in which the replication of the pathogens possibly present occurs; and
    a mass spectrophotometer that is configured to identify the pathogens in at least an aliquot of the liquid culture medium containing the biological sample, which has reached a desired turbidity value and/or a desired concentration of the pathogens according to a standardized scale of values, said mass spectrophotometer is further configured for calibration on the basis of the results of the measurement of the turbidity and/or concentration of the pathogens obtained by the apparatus that is configured to measure and continuously monitor a turbidity and/or the concentration of the pathogens;
    wherein said apparatus that is configured to measure and continuously monitor a turbidity and/or the concentration of the pathogens comprises a processor and a memory in which a first data (D1) and a second data (D2) are stored,
    wherein the first data (D1) relates to a predefined graduated progression of turbidity values and/or concentration of the pathogens, and the second data (D2) relates to a defined correlation between said turbidity values and/or concentration of the pathogens and ranges in weight of the pathogens loaded in the biological sample the defined correlation being suitable for the functioning of the mass spectrophotometer, said processor being configured to select said desired turbidity value and/or the desired concentration of the pathogens among said first data (D1) on the basis of one of the values contained in said second data (D2) which is selected on each occasion on the basis of the specific needs of said mass spectrophotometer, wherein said apparatus that is configured to measure and continuously monitor a turbidity and/or the concentration of the pathogens is further configured to obtain a desired turbidity value and/or a desired concentration of pathogen which are responsible for the infection in a time period that is shorter than that of other contaminating pathogens, a time needed for pathogens to adapt to the environment in said biological sample and to manifest growth being shorter for the pathogens that are responsible for the infection than that of the other contaminating pathogens such that the identification by the mass spectrophotometer is independent from the presence of said other contaminating pathogens in the biological sample.

7. The method as in claim 1, wherein the time needed to obtain the desired turbidity value and/or the desired concentration of the pathogens in the first step is between 45 minutes and 3 hours.

8. The method as in claim 1, wherein at least one selected from the group consisting of light-scattering technology, nephelometric laser techniques, photometric reading systems optoelectronic or radio frequency, and ultrasound techniques is used in said first step.

9. The apparatus as in claim 6, wherein the time needed to obtain the desired turbidity value and/or the desired concentration of the pathogens in the first step is calculated based on a known lag phase in a growth of said other contaminating pathogens in the biological sample due to an adjustment of said other contaminating pathogens to a grown environment in said biological sample.

10. The apparatus as in claim 6, wherein the time needed to obtain the desired turbidity and/or the desired concentration of the pathogens is between 45 minutes and 3 hours.

11. The apparatus as in claim 6, wherein the apparatus that is configured to measure and continuously monitor a turbidity and/or the concentration of the pathogens includes at least one selected from the group consisting of a light-scattering technology device, a nephelometric laser technique device, a photometric reading system, an optoelectronic device, a radio frequency device, and an ultrasound device.

12. The method as in claim 1, wherein said standardization value scale is the McFarland turbidity scale.

13. The apparatus as in claim 6, wherein said standardized value scale is the McFarland turbidity scale.

* * * * *